(12) United States Patent
Teraura

(10) Patent No.: US 10,478,541 B2
(45) Date of Patent: Nov. 19, 2019

(54) CENTRIFUGAL PUMP FOR MEDICAL USE AND ARTIFICIAL HEART ASSIST DEVICE HAVING CENTRIFUGAL PUMP FOR MEDICAL USE

(71) Applicant: HI-LEX CORPORATION, Hyogo (JP)

(72) Inventor: Makoto Teraura, Hyogo (JP)

(73) Assignee: HI-LEX CORPORATION, Hyogo (JP)

( * ) Notice: Subject to any disclaimer, the term of this patent is extended or adjusted under 35 U.S.C. 154(b) by 0 days.

(21) Appl. No.: 15/513,816

(22) PCT Filed: Sep. 24, 2015

(86) PCT No.: PCT/JP2015/076925
§ 371 (c)(1),
(2) Date: Mar. 23, 2017

(87) PCT Pub. No.: WO2016/047687
PCT Pub. Date: Mar. 31, 2016

(65) Prior Publication Data
US 2017/0296721 A1 Oct. 19, 2017

(30) Foreign Application Priority Data

Sep. 26, 2014 (JP) ................................ 2014-196766

(51) Int. Cl.
*A61M 1/10* (2006.01)
*F04D 7/04* (2006.01)
(Continued)

(52) U.S. Cl.
CPC ........ *A61M 1/1029* (2014.02); *A61M 1/1012* (2014.02); *A61M 1/122* (2014.02);
(Continued)

(58) Field of Classification Search
CPC .. A61M 1/1029; A61M 1/1012; A61M 1/122; A61M 1/3666; A61M 2205/3606;
(Continued)

(56) References Cited

U.S. PATENT DOCUMENTS 6,152,704 A * 11/2000 Aboul-Hosn ........... F04D 13/04
417/360
6,719,791 B1 * 4/2004 Nusser ..................... F16J 15/43
415/900

FOREIGN PATENT DOCUMENTS

CN 202236531 U 5/2012
JP H04-017862 1/1992
(Continued)

OTHER PUBLICATIONS

Jan. 17, 2019, German Office Action issued for related DE Application No. 112015004388.8.

*Primary Examiner* — Christopher Koharski
*Assistant Examiner* — Roland Dinga
(74) *Attorney, Agent, or Firm* — Paratus Law Group, PLLC

(57) ABSTRACT

A centrifugal pump includes a rotating shaft, a pump substrate, a housing and an impeller. The pump substrate has a driving unit configured to rotate the rotating shaft. The housing has an inlet and an outlet and forms a pump chamber with the pump substrate. A body fluid sucked from the inlet flows through the pump chamber. The impeller is housed in the pump chamber and is configured to use the rotating shaft as an axis. The pump substrate has a magnetism generating source. The rotating shaft protrudes into the pump chamber from the pump substrate, and is pivotally supported on the pump substrate. A magnetic fluid is disposed on at least one of spaces formed among the pump substrate, the rotating shaft, and the impeller.

6 Claims, 2 Drawing Sheets

(51) Int. Cl.
*F04D 29/16* (2006.01)
*A61M 1/12* (2006.01)
*A61M 1/36* (2006.01)
*F04D 13/02* (2006.01)

(52) U.S. Cl.
CPC ............ *A61M 1/3666* (2013.01); *F04D 7/04* (2013.01); *F04D 29/167* (2013.01); *A61M 1/101* (2013.01); *A61M 1/102* (2014.02); *A61M 2205/366* (2013.01); *A61M 2205/3606* (2013.01); *F04D 13/024* (2013.01); *F05D 2300/507* (2013.01)

(58) Field of Classification Search
CPC .. A61M 2205/366; F04D 7/04; F04D 29/167; F05D 2300/507
USPC .......................................................... 607/16
See application file for complete search history.

(56) References Cited

FOREIGN PATENT DOCUMENTS

| | | |
|---|---|---|
| JP | H09-206372 | 8/1997 |
| WO | WO00/062841 A1 | 10/2000 |
| WO | WO 2014/019646 A1 | 2/2014 |

\* cited by examiner

CENTRIFUGAL PUMP FOR MEDICAL USE AND ARTIFICIAL HEART ASSIST DEVICE HAVING CENTRIFUGAL PUMP FOR MEDICAL USE

CROSS REFERENCE TO PRIOR APPLICATION

This application is a National Stage Patent Application of PCT International Patent Application No. PCT/JP2015/076925 (filed on Sep. 24, 2015) under 35 U.S.C. § 371, which claims priority to Japanese Patent Application No. 2014-196766 (filed on Sep. 26, 2014), which are all hereby incorporated by reference in their entirety.

TECHNICAL FIELD

The present invention relates to a centrifugal pump for medical use and an artificial heart assist device having the centrifugal pump for medical use.

BACKGROUND ART

A blood pump device such as an artificial heart assist device has been known as a device for assisting circulation of blood of a patient who has suffered from malfunction or the like of an organ such as a heart. There are various kinds of blood pump devices. For example, there is a blood pump device in which a centrifugal pump is used for sucking and discharging a fluid by a centrifugal force caused by a rotation of an impeller. As an example of the centrifugal pump-typed blood pump device, a centrifugal blood pump device is disclosed in Patent Document 1 which includes a housing having a blood inlet port and a blood outlet port and an impeller that rotates in the housing and feeds blood using a centrifugal force in rotating.

CITATION LIST

Patent Document

Patent Document 1: JP-A-09-206372

SUMMARY OF THE INVENTION

Problems to be Solved by the Invention

However, a body fluid such as blood contains proteins. The proteins enter a space between an impeller and an inner wall of a pump chamber or a space between an impeller and a shaft of a pump chamber, by heat generated due to the rotation of the impeller, resulting in being thermally denatured, and thus rotation defects of the impeller may occur. That is, when the blood enters the narrow space between the impeller and the inner wall of the pump chamber and the proteins contained in the blood are thermally denatured, by heat of an electric motor for rotating the impeller or friction during the rotation of the impeller, in the narrow space, the impeller may hardly rotate. Therefore, it is necessary to reduce the rotation defects of the impeller.

The present invention has been made in view of the above problems and an object thereof is to provide a centrifugal pump for medical use and an artificial heart assist device, thereby preventing rotation defects due to thermal denaturation of proteins.

Means for Solving the Problems

A centrifugal pump for medical use according to the present invention, including: a rotating shaft; a pump substrate that has a driving unit configured to rotate the rotating shaft; a housing that has an inlet and an outlet and that forms a pump chamber with the pump substrate, the pump chamber through which a body fluid sucked from the inlet flows; and an impeller that is housed in the pump chamber and that is configured to use the rotating shaft as an axis, characterized in that, the pump substrate has a magnetism generating source, the rotating shaft protrudes into the pump chamber from the pump substrate, and is pivotally supported on the pump substrate, and a magnetic fluid is disposed on at least one of spaces formed among the pump substrate, the rotating shaft and the impeller.

Preferably, the driving unit may be a motor, and the magnetism generating source may be the motor.

Preferably, the magnetic fluid may be disposed on an outer periphery side of the impeller in the space formed between the pump substrate and the impeller.

In addition, an artificial heart assist device according to the present invention is characterized by including the centrifugal pump for medical use, in which the driving unit is a motor, and the pump substrate and the housing can be implanted in a human body.

Effects of the Invention

According to the centrifugal pump for medical use and the artificial heart assist device of the present invention, it is possible to prevent rotation defects of the impeller due to the thermal denaturation of the proteins by sealing the space formed by the impeller with the magnetic fluid.

EMBODIMENTS FOR CARRYING OUT THE INVENTION

Figure 1:
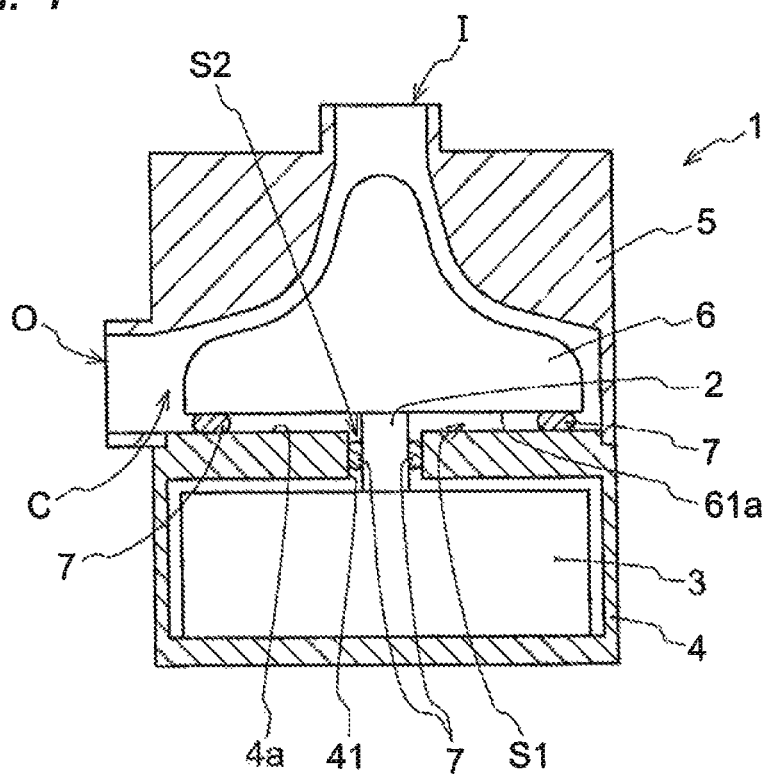
FIG. 1 It is a partial cross-sectional view schematically illustrating centrifugal pump for medical use according to an embodiment of the present invention.

Referring to the drawings, a centrifugal pump for medical use and an artificial heart assist device according to the present invention will be described in detail below.

As illustrated in FIG. 1, a centrifugal pump for medical use 1 according to an embodiment of the present invention includes a rotating shaft 2, a pump substrate 4 that has a driving unit 3 configured to rotate the rotating shaft 2, a housing 5 that has an inlet I and an outlet O and that forms a pump chamber C with the pump substrate 4, the pump chamber C through which a body fluid sucked from the inlet I flows, and an impeller 6 that is housed in the pump chamber C and is configured to use the rotating shaft 2 as an axis.

The centrifugal pump for medical use 1 discharges the body fluid, which is sucked from the inlet I, from the outlet O, and delivers the body fluid such as blood. The centrifugal pump for medical use 1 can be used for circulating the body fluid such as blood in, for example, an artificial heart assist device or an artificial heart-lung machine. When the artificial heart assist device has the centrifugal pump for medical use 1, it can be an implantable-type artificial heart assist device in which the driving unit 3 is used as a motor and the pump substrate 4 and the housing 5 can be implanted in a human body.

The pump substrate 4 houses the driving unit 3 of the centrifugal pump for medical use 1. The driving unit 3 is, for example, an electric motor, and generates a rotational force by a rotor (not illustrated) driven by a magnetic force, thereby rotating the rotating shaft 2. The pump substrate 4 has a rotating shaft insertion portion 41 through which the rotating shaft 2 is inserted, and the rotating shaft 2 inserted through the rotating shaft insertion portion 41 protrudes into the pump chamber C from the pump substrate 4. For example, the rotating shaft 2 is pivotally supported on the pump substrate 4 by a bearing (not illustrated) or the like.

Figure 2:
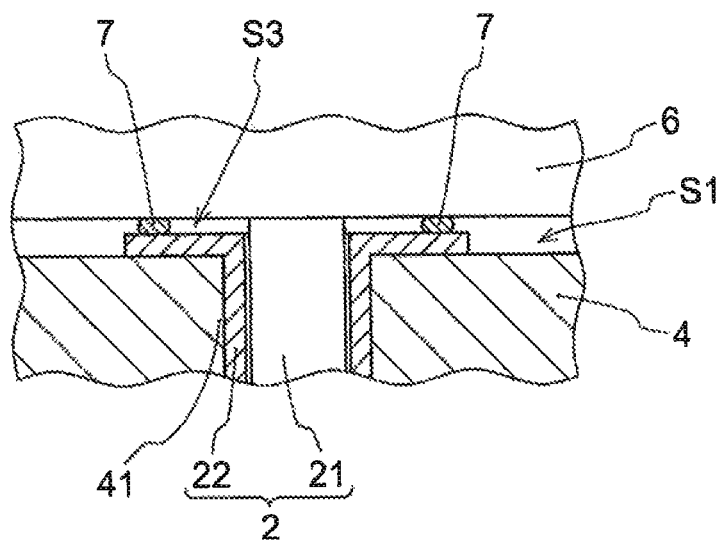
FIG. 2 It is a partial cross-sectional view schematically illustrating a part of a centrifugal pump for medical use according to another embodiment of the present invention, in which a magnetic fluid is disposed between a rotating shaft having a dual structure and an impeller.

When the rotating shaft 2 protruding into the pump chamber C is driven by the driving unit 3, the impeller 6 rotates. The rotating shaft 2 and the impeller 6 may be formed integrally with each, or may be connected to each other after being separately formed. In addition, the rotating shaft 2 may have a solid inside or a hollow inside as long as rotating with the driving of the driving unit 3. Further, as illustrated in FIG. 2, the rotating shaft 2 may have a dual structure including a shaft body 21 and a cylindrical body 22 formed around the shaft body 21, and may be inserted through the rotating shaft insertion portion 41 of the pump substrate 4, with the structure that the shaft body 21 rotates around the inside of the cylindrical body 22.

The pump substrate 4 is formed of a magnetically permeable non-magnetic material. The pump substrate 4 is formed in a substantially cylindrical shape in the embodiment illustrated in FIGS. 1 and 3, but the pump substrate 4 may have various shapes without being limited thereto. In addition, a top surface 4a (a surface facing a bottom surface 61a of a base portion 61 of the impeller 6) of the pump substrate 4 serving as a part of the pump chamber C has a flat surface as illustrated in FIG. 1, but may be inclined depending on the shape of the impeller 6.

Together with the pump substrate 4, the housing 5 forms the pump chamber C into which the body fluid such as blood flows. For example, the pump chamber C may be formed by connection of the housing 5 and the pump substrate 4 in a liquid-tight manner, or may be formed by integration of the housing 5 with the pump substrate 4. In this embodiment, the housing 5 has the inlet I for sucking the body fluid into the pump chamber C and the outlet O through which the body fluid sucked from the inlet I is delivered by the impeller 6, and the pump chamber C is formed between the inlet I and the outlet O. The shape of the housing 5 is not particularly limited as long as it has the inlet I and the outlet O and the pump chamber can be formed to house the impeller 6 and to exert a target function of being filled with the body fluid such as blood.

Figure 3:
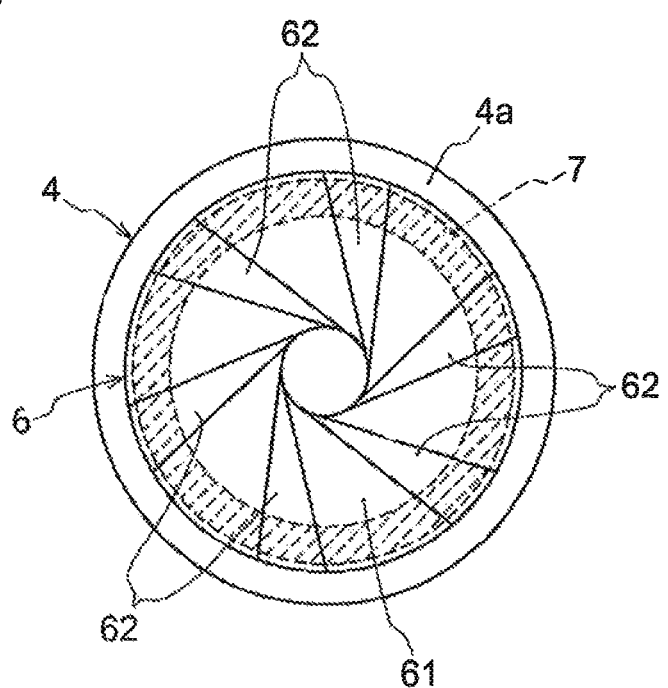
FIG. 3 It is a top view of a pump substrate and the impeller as seen from an upper side in a state in which a housing of the centrifugal pump for medical use illustrated in FIG. 1 is removed.

The impeller 6 housed in the pump chamber C delivers the body fluid, which flows from the inlet I, from the outlet O. The impeller 6 rotates around the rotating shaft 2 as the rotating shaft 2 rotates by the driving unit 3. In this embodiment, as illustrated in FIG. 3, the impeller 6 includes the base portion 61 having substantially a disk shape and facing the top surface 4a of the pump substrate 4 and blades 62 provided on the base portion 61, and the body fluid is delivered to the outlet O by the blades 62 when the impeller 6 rotates. The shape of the base portion 61 of the impeller 6 or the shape and number of the blades 62 of the impeller 6 are not limited to the embodiment illustrated in FIGS. 1 and 3.

In the centrifugal pump for medical use 1 in which the impeller 6 is disposed in the pump chamber C, spaces are formed among the pump substrate 4, the rotating shaft 2, and the impeller 6; that is, a space S1 is formed between the pump substrate 4 and the impeller 6, a space S2 is formed between the pump substrate 4 and the rotating shaft 2, and a space S3 (see FIG. 2) may be formed between the rotating shaft 2 and the impeller 6 when the rotating shaft 2 has the dual structure as illustrated in FIG. 2, for example. In the case of having a mechanical seal member, a slight space (for example, 0.5 to 2.5 µm) is required to be formed in particular between two rotating members provided among the pump substrate 4, the rotating shaft 2, and the impeller 6. The body fluid containing proteins such as blood may intrude into these spaces. Therefore, the centrifugal pump for medical use 1 according to the embodiment of the present invention has a configuration in which the pump substrate 4 has a magnetism generating source and the magnetic fluid 7 is disposed in at least one of the spaces formed among the pump substrate 4, the rotating shaft 2, and the impeller 6.

The magnetic fluid 7 is attracted by the magnetism generating source of the pump substrate 4, and at predetermined positions, seals the spaces formed among the pump substrate 4, the rotating shaft 2, and the impeller 6 or the space formed between the rotating seal members provided therebetween. The magnetic fluid 7 may seal the spaces so as to prevent components to be fixed by heat, for example, proteins of the body fluid from intruding into the spaces. For example, as illustrated in FIG. 3, it is preferable to dispose the magnetism generating source so that the magnetic fluid 7 is annularly disposed. As the magnetism generating source, for example, when the driving unit 3 is a motor, the motor can be used as the magnetism generating source. The housing 5 and/or the pump substrate 4 can be formed of a non-magnetic material so as not to affect the relation of a magnetic force between the magnetic fluid 7 and the magnetism generating source.

The magnetism generating source adsorbs the magnetic fluid 7 at a predetermined position, at which the sealing is required, for example, using a permanent magnet (or electromagnet) to be used for the motor, and thus at least one or all of the spaces S1 to S3 can be sealed. Therefore, it is possible to suppress the body fluid such as blood flowing into the pump chamber C from intruding into the spaces S1 to S3. Accordingly it is possible to suppress an increase in resistance against the rotation of the impeller 6 due to the thermal denaturation of a substance derived from the body fluid containing proteins, and to suppress rotation defects of the impeller 6 or a decrease in a flow rate of the body fluid delivered from the outlet O. Normally, the spaces are very narrow which are formed among the pump substrate 4, the rotating shaft 2, and the impeller 6 in the pump chamber C, and the amount of body fluid such as blood entering the spaces is too small to circulate. Thus, heat can hardly be dispersed, and the thermal denaturation of the proteins easily occurs compared to a case where a large amount of body fluid circulates. When the body fluid is suppressed from entering the very narrow spaces, it is possible to prevent rotation defects of the impeller 6 due to the thermal denaturation of the proteins and provide the centrifugal pump for medical use 1 with more safety.

Furthermore, as illustrated in FIGS. 1 and 3, the magnetic fluid 7 is preferably disposed on an outer periphery side of the impeller 6 in the space S1 formed between the pump substrate 4 and the impeller 6. In this case, since the amount of body fluid entering the space S1 can be further reduced, the possibility of the thermal denaturation of the proteins can be further reduced. In order to dispose the magnetic fluid 7 on the outer periphery side of the impeller 6, for example, a magnetism generating source such as a permanent magnet may be provided at a position facing the outer periphery side of the bottom surface 61a of the impeller 6. The motor is used as the magnetism generating source in the above-described embodiments, but a magnetism generating source such as a permanent magnet may be disposed separately from the motor at a predetermined position of the pump substrate 4.

In addition, a leakage suppressing portion may be provided in the pump substrate 4 and/or the impeller 6 to suppress leakage of the magnetic fluid 7 from the space S1. When the leakage suppressing portion is provided, it is possible to suppress the leakage of the magnetic fluid 7 from the space S1 and the circulation of the magnetic fluid 7 in a state of being mixed with the body fluid such as blood. The leakage of the magnetic fluid 7 may be prevented by a physical way such as a projection, which is annularly provided toward the top surface 4a of the pump substrate 4 at an outer circumferential edge of the bottom surface 61a of the base portion 61, as the leakage suppressing portion, or the leakage of the magnetic fluid 7 may be prevented by disposing a magnetic body to be controlled by a magnetic force.

In addition, a supply path may be provided through which a circulating coolant for cooling heat caused by the impeller or the motor is supplied to the pump substrate 4. When the circulating coolant is supplied to a boundary between the impeller 6 and the rotating shaft 2, the magnetic fluid 7 may seal a position serving as a boundary surface between the body fluid and the circulating coolant. In this case, the body fluid and the circulating coolant can be sealed, and thus, components of the coolant can also be prevented from being mixed into the body fluid.

EXPLANATIONS OF LETTERS OR NUMERALS

1: Centrifugal pump for medical use
2: Rotating shaft
21: Shaft body
22: Cylindrical body
3: Driving unit
4: Pump substrate
41: Rotating shaft insertion portion
4a: Top surface of pump substrate
5: Housing
6: Impeller
61: Base portion
61a: Bottom surface
62: Blade
7: Magnetic fluid
C: Pump chamber
I: Inlet
O: Outlet
S1: Space between pump substrate and impeller
S2: Space between pump substrate and rotating shaft
S3: Space between rotating shaft and impeller

The invention claimed is:

1. A centrifugal pump for medical use, comprising:
a rotating shaft;
a pump substrate that has a driving unit configured to rotate the rotating shaft;
a housing that has an inlet and an outlet and that forms a pump chamber with the pump substrate, the pump chamber through which a body fluid sucked from the inlet flows; and
an impeller that is housed in the pump chamber and that is configured to use the rotating shaft as an axis,
wherein the pump substrate has a magnetism generating source,
the rotating shaft protrudes into the pump chamber from the pump substrate, and is pivotally supported on the pump substrate,
a space is formed between the pump substrate and the impeller and a space is formed between the pump substrate and the rotating shaft, and
a magnetic fluid is configured to seal an outer periphery side of the impeller in the space formed between the pump substrate and the impeller.

2. The centrifugal pump for medical use according to claim 1,
wherein the driving unit is a motor, and
the magnetism generating source is the motor.

3. An artificial heart assist device having the centrifugal pump for medical use according to claim 2,
wherein the pump substrate and the housing are capable of being implanted in a human body.

4. An artificial heart assist device having the centrifugal pump for medical use according to claim 1,
wherein the driving unit is a motor, and
the pump substrate and the housing are capable of being implanted in a human body.

5. The centrifugal pump for medical use according to claim 1,
wherein a space is formed between the rotating shaft and the impeller when the rotating shaft has a dual structure.

6. The centrifugal pump for medical use according to claim 1,
wherein the magnetism generating source is provided at a position facing the outer periphery side of the impeller.

* * * * *